United States Patent [19]

Shinohara et al.

[11] 4,299,627
[45] Nov. 10, 1981

[54] METHOD OF MANUFACTURING OXYGEN SENSING ELEMENT

[75] Inventors: Hiroshi Shinohara, Okazaki; Yasuhiro Otsuka, Toyota; Shinichi Matsumoto, Toyota; Toshinobu Furutani, Toyota; Hiroshi Wakizaka, Toyota, all of Japan

[73] Assignee: Toyota Jidosha Kogyo Kabushiki Kaisha, Toyota, Japan

[21] Appl. No.: 72,822

[22] Filed: Sep. 6, 1979

[30] Foreign Application Priority Data

Sep. 11, 1978 [JP] Japan .............................. 53-110605

[51] Int. Cl.$^3$ ............................ B22F 3/00; B22F 7/00
[52] U.S. Cl. ................................. 75/206; 75/208 R; 428/557
[58] Field of Search .............. 428/557; 75/208 R, 206

[56] References Cited

U.S. PATENT DOCUMENTS

| | | | |
|---|---|---|---|
| 2,673,277 | 3/1954 | Lemmens et al. | 428/557 |
| 3,161,504 | 12/1964 | Black et al. | 75/208 R |
| 3,248,214 | 4/1966 | Kroeger et al. | 75/208 R |
| 3,489,554 | 1/1970 | Waldo | 75/208 R |
| 3,809,552 | 5/1974 | Klein | 75/208 R |

Primary Examiner—Brooks H. Hunt
Attorney, Agent, or Firm—Kenyon & Kenyon

[57] ABSTRACT

An oxygen sensing element capable of measuring partial pressures of oxygen in sample gases, which element has a solid electrolyte member having totally embedded therein a means for providing a reference partial pressure of oxygen composed of a sintered product of a finely divided metal or metal-metal oxide mixture and having a lead-out wire connected thereto is prepared by a method wherein:

(a) a part of the finely divided solid electrolyte material is compression-moded to form a provisional solid electrolyte member having a hole;

(b) a provisional product of the reference oxygen partial pressure-providing means is formed in the hole of the provisional solid electrolyte member from the finely divided metal or metal-metal oxide mixture;

(c) the remaining part of the finely divided solid electrolyte material is piled up on the provisional reference oxygen partial pressure-providing means product, followed by compression molding the piled up solid electrolyte material to form an integrated structure comprising the solid electrolyte member having totally embedded therein the provisional reference oxygen partial pressure-providing means;

(d) the integrated structure is sintered in a non-oxidizing atmosphere at approximately 1,350° to 1,500° C.; and, (e) a layer or layers of an external conductive metal electrode or electrodes is formed on at least a part of the exterior surface of the sintered product.

6 Claims, 9 Drawing Figures

METHOD OF MANUFACTURING OXYGEN SENSING ELEMENT

BACKGROUND OF THE INVENTION

This invention relates to a method of manufacturing an oxygen sensing element capable of measuring partial pressures of oxygen in sample gases. The oxygen sensor device is suitable for use in detecting the concentration of oxygen in an exhaust gas from an internal combustion engine of an automobile. It is particularly suitable for use in an exhaust gas purifying system wherein the concentration of oxygen in the exhaust gas is measured, thereby to determine the contents of unburnt hydrocarbons, carbon monoxide and nitrogen oxides in the exhaust gas, and based on the measurement results, the air-fuel ratio is appropriately adjusted so that the efficiency of a catalyst for purifying the exhaust gas is enhanced.

An oxygen sensor is an oxygen concentration cell which has electrodes mounted on the opposite sides of a solid electrolyte composed of a sintered ceramic material capable of conducting an oxygen ion, such as, for example, zirconia stabilized with a minor proportion of $Y_2O_3$, CaO or MgO. An electromotive force is produced across the solid electrolyte by the difference between the partial pressures of oxygen in a reference gas and an exhaust gas, contacting opposite sides of the solid electrolyte. The concentration of oxygen in the exhaust gas can be determined by measuring the electromotive force as produced. Conventionally, air is used as the reference gas. The reference gas may also be generated chemically by using a mixture of a metal and its oxide (for example, a mixture of iron and iron oxide) which produces an equilibrium partial pressure of oxygen. Such a metal-metal oxide mixture is hereinafter referred to as "reference solid electrode" for brevity.

An oxygen sensing cell or element has a structure of the type wherein air is introduced or a reference solid electrode is enclosed in a solid electrolyte member of a tubular form, one end of which is closed, or a cup form; an electrode layer composed of an electrochemically active metal, such as platinum, is provided on the interface between the reference solid electrode or air and the solid electrolyte member, and; an external conductive metal electrode or electrodes to be exposed to the exhaust gas are mounted on the exterior surface of the solid electrolyte member. However, this oxygen sensing element is not advantageous for the following reasons. First, it is difficult or complicated to form a uniform electrode layer on the interface between the reference solid electrode or air and the solid electrolyte member, and thus, it is difficult to avoid variability in some performances, such as the operating temperature, the response time and the internal resistance among the resulting sensing elements. Secondly, it is also difficult to form a durable seal in the upper opening of the cup-shaped or tubular sensing element, and thus, it is difficult to maintain a constant partial pressure of oxygen generated by the reference solid electrode over a long period of time.

Another oxygen sensing element is of a short columnar shape and has a structure such that a reference solid electrode is completely embedded or enclosed within a solid electrolyte member, and; two external conductive metal electrodes are mounted on the exterior surface of the solid electrolyte member, one of the electrodes being exposed to the exhaust gas and the other being connected to the reference solid electrode through a lead-out wire extending in a radial direction within the solid electrolyte member. Such an oxygen sensing element is disclosed in Japanese Patent Publication (KOKAI) No. 9,497/1976. It is presumed that this oxygen sensing element does not possess the defects mentioned in the preceding paragraph. It is mentioned in that Japanese patent publication that the solid electrolyte member is formed about the reference solid electrode by chemical vapor deposition, ion plating, sintering or sputtering. However, the Japanese patent publication is silent on the particulars of the method of manufacturing the oxygen sensing element and, in actuality, some difficulties are encountered in the course of its manufacture. For example, when it is intended to manufacture the oxygen sensing element by sintering, it is difficult to obtain a molded product to be sintered. That is, in the step of press molding the finely divided solid electrolyte material, intrusion of the finely divided material into a minute gap between the lead-out wire and the groove on the mold for the lead-out wire cannot be completely avoided. Such intrusion makes it difficult to release the lead-out wire from the mold, and upon releasing, imposes a stress on the lead-out wire and on the portion of the molded product surrounding the lead-out wire. Due to the stress, this portion of the molded product is poor in sintering characteristics as compared with the remainder of the molded product. Thus, the molded product is liable to be cracked upon sintering, and the sintered product is not homogeneous and is poor in airtightness in the portion of the sintered product contacting the lead-out wire.

SUMMARY OF THE INVENTION

It is a main object of the present invention to provide a method of manufacturing an oxygen sensing element having a structure such that a reference solid electrode having a lead-out wire connected thereto is totally embedded in a solid electrolyte member, which element is composed of a uniformly sintered product having no cracks and exhibiting good airtightness in the portion thereof contacting the lead-out wire.

The method of the present invention comprises the steps of:

(a) compression molding a part of the finely divided solid electrolyte material to form a provisional solid electrolyte member having a hole in which a reference solid electrode is to be formed;

(b) forming in said hole of the provisional solid electrolyte member a provisional product of the reference solid electrode from the finely divided metal or metal-metal oxide mixture;

(c) piling up the remaining part of the finely divided solid electrolyte material on the upper surface of the provisional reference solid electrode product and on the upper surface of the provisional solid electrolyte member, followed by compression molding the piled up solid electrolyte material to form an integrated structure comprising the solid electrolyte member having totally embedded therein the provisional reference solid electrode;

(d) sintering the integrated structure, in a non-oxidizing atmosphere, at a temperature of from 1,350° C. to 1,500° C., and;

(e) forming a layer or layers of the external conductive metal electrode or electrodes on at least a part of the exterior surface of the sintered integrated structure.

BRIEF DESCRIPTION OF THE INVENTION

The invention will be described with reference to the accompanying drawings, wherein.

Figure 5:
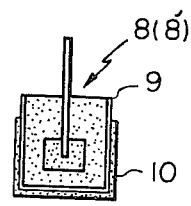
Figure 6A:
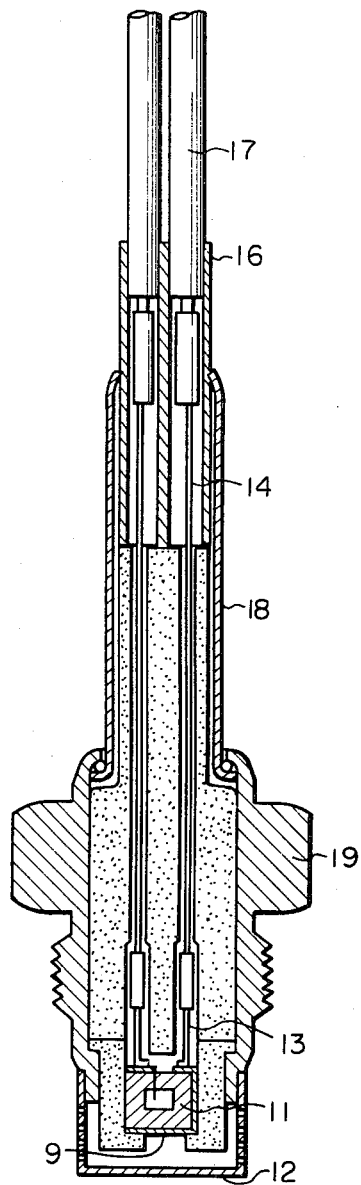
Figure 6B:
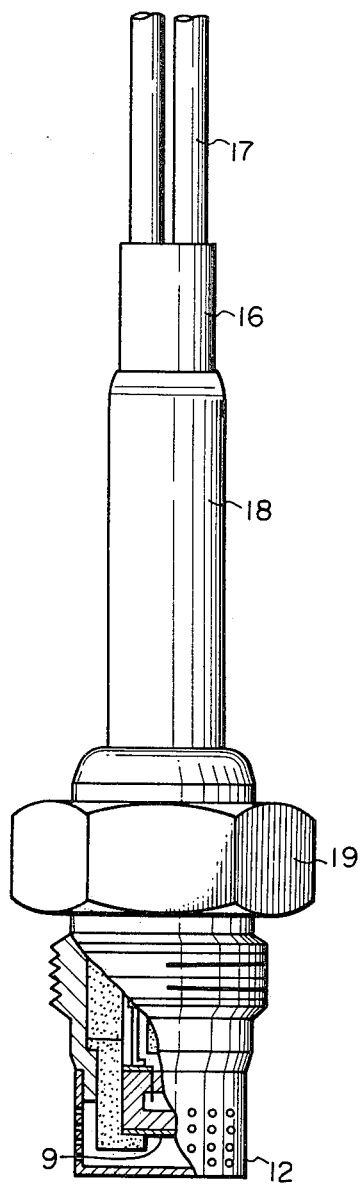

FIG. 5 illustrates the steps of forming an external metal electrode layer on a part of a sintered product, and then, forming a porous spinel protective coating layer thereon, FIG. 6A is a sectional view illustrating an oxygen sensor device provided with the oxygen-sensing element of the invention, which device is for use in detection of the concentration of oxygen in an exhaust gas from an automobile internal combustion engine, and;

FIG. 6B is an elevational view partly in section illustrating the oxygen sensor device illustrated in FIG. 6A.

DESCRIPTION OF THE PREFERRED EMBODIMENT

Figure 1:
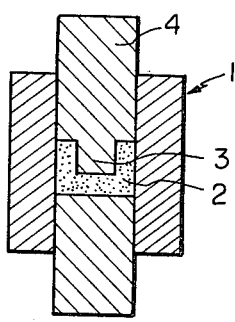
FIG. 1 illustrates a step of forming a provisional solid electrolyte member.

Referring to FIG. 1, a finely divided solid electrolyte material 2, for example, a finely divided zirconia (ZrO) powder stabilized by having incorporated therein a minor amount of $Y_2O_3$, CaO or MgO, is placed within a cylindrical mold 1. Then, a plunging rod 4, provided with a projection 3 at the lowermost end thereof, is thrust into the mold 2 to consolidate the finely divided solid electrolyte material, whereby a provisional solid electrolyte member having a hole is formed within the mold 1. The projection 3 of the plunging rod 4 has a shape corresponding to a predominant part or the entire body of a solid electrolyte member to be formed in the hole of the provisional solid electrolyte member. The plunging pump can be thrust into the mold 1 at a pressure of from approximately 300 to 1,500 kg/cm² by using, for example, a hand press.

Figure 2:
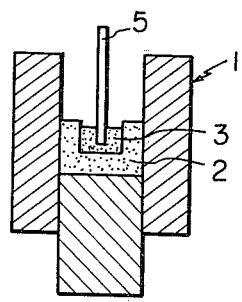
FIG. 2 illustrates a step of forming a provisional product of a reference solid electrode.

Thereafter, the hole of the provisional solid electrolyte member 2 is charged with a finely divided metal powder or a mixture of a finely divided metal powder and a finely divided metal oxide powder (the metal ingredient of which metal oxide is the same as that of the metal powder), and then, the charged metal powder or metal-metal oxide powder is consolidated in a manner similar to that employed for the formation of the provisional solid electrolyte member 3, whereby a provisional product of a reference solid electrode is formed as illustrated in FIG. 2. Alternatively, a provisional product of a reference solid electrode is compression-molded from a metal powder or a metal-metal oxide mixed powder by using another mold, and the so molded product is inserted into the hole of the provisional solid electrolyte member. Thereafter, a suitable length of a lead-out wire 5 is fixed in the provisional product of a reference solid electrode as illustrated in FIG. 2.

Figure 3A:
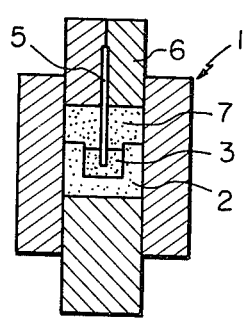
FIGS. 3A and 3B illustrate alternative steps of forming an integrated structure of the solid electrolyte member having embedded therein the provisional reference solid electrode.
Figure 4A:
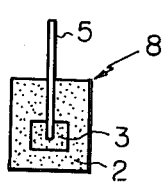
FIGS. 4A and 4B illustrate products formed by the step illustrated in FIGS. 3A and 3B, respectively.

As illustrated in FIG. 3A, an additional amount of a finely divided solid electrolyte material 7 is piled up on the upper surface of the provisional reference solid electrode product 3 and on the upper surface of the provisional solid electrolyte member 2, and then, the piled up material 7 is compressed by a pair of split plunging rods 6. The split plunging rods 6 have a narrow space formed therebetween in which the lead-out wire 5 is fitted. The molded product 8 so obtained is of a structure such that a reference solid electrode product 3 is totally embedded in a solid electrolyte 2 as illustrated in FIG. 4A.

Figure 3B:
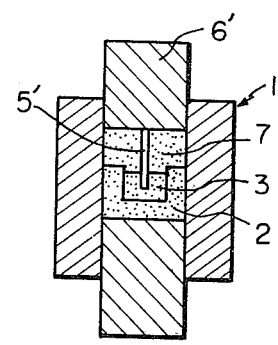
Figure 4B:
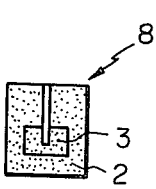

Alternatively, the hole of the provisional solid electrolyte member 2 within the mold 1 is charged with a finely divided metal powder or a finely divided metal-metal oxide mixed powder 3 and then, if desired, the charged metal or metal-metal oxide mixed powder is consolidated. Or, a finely divided metal powder or a finely divided metal-metal oxide powder is compression-molded into a provisional reference solid electrode product by using another mold, and the so molded product is inserted into the hole of the provisional solid electrolyte member 2. Thereafter, an additional amount of a finely divided solid electrolyte material 7 is piled up on the upper surface of the charged metal or metal-metal oxide mixed powder 3 or the consolidated metal or metal-oxide mixed powder 3 or the inserted provisional reference solid electrode product. Then, as illustrated in FIG. 3B, a lead-out wire 5' of the desired length (which is such that one end of the wire 5' does not protrude from a solid electrode to be formed) is inserted in the piled solid electrolyte material 7. Thereafter, a plunger rod 6' is thrust into the mold 1. The molded structure 8' so obtained is illustrated in FIG. 4B.

The molded product 8 or 8' is then sintered in a non-oxidizing atmosphere at a temperature of from approximately 1,350° to 1,500° C. The sintering may be effected by using an electric furnace or other conventional furnaces. As the non-oxidizing gas, an inert gas such as argon or nitrogen, or a mixture of such an inert gas and a minor amount of a reducing gas such as hydrogen may be used. The sintering time may be varied depending upon the sintering temperature, the solid electrolyte material and the reference solid electrode material. Usually, the sintering time is in the range of from one to six hours.

Thereafter, as illustrated in FIG. 5, a layer or layers of an external conductive metal electrode or electrodes 9 to be exposed to a sample gas is formed on at least a part of the exterior surface of the sintered product 8 or 8'. The formation of the external conductive metal electrode layer or layers 9 may be effected by a process wherein the exterior surface of the sintered product is polished, degreased and then, washed, and finally, a thermally resistant, electrically conductive metal such as platinum or a platinum-rhodium alloy is applied to the exterior surface by a conventional technique such as paste coating and baking, electroplating or chemical plating or ion plating, by using a thermal-resistant conductive material such as platinum or a platinum-rhodium alloy. It is preferable that the external electrode 9, so formed, to be exposed to a sample gas be coated with a porous layer having a magnesium spinel structure or another spinel structure composed of a thermal resistant metal oxide such as α-alumina. Such a porous layer may be formed by a conventional technique, such as a flame spraying technique. The porous layer minimizes the deterioration of the porous external electrode 9 caused by the phosphorus, lead and sulfur present in the exhaust gas from an automobile.

The oxygen sensing element 1 may be of any desired shape, such as, for example, a disc, column, sphere or parallelopiped. Of these, a disc and column are desirable. It is preferable that the lead-out wire 5 or 5' (in FIG. 3A or 3B) is fixed in the disc or columnar oxygen sensing element so that the lead-out wire is consistent with or in parallel with the axis of the oxygen sensing element.

The solid electrolyte member may be composed of a solid electrolyte material conventionally used in oxygen concentration cells, such as zirconia ($ZrO_2$). The solid electrolyte material is preferably a solid solution prepared by incorporating a minor amount of $Y_2O_3$, CaO or MgO followed by sintering. An optimum solid electrolyte material is comprised of a sintered zirconia composition having incorporated therein 4 to 10% by mole of $Y_2O_3$.

The reference solid electrode is a sintered product of a finely divided metal or metal-metal oxide mixture powder. Even when the reference solid electrode is not made of a metal-metal oxide mixture but only metal, it can provide a reference partial pressure of oxygen, because the reference solid electrode accepts oxygen ions transmitted through the solid electrolyte material during the operation of the oxygen sensing element and, thus, the metal is partially converted into metal oxide. The metal ingredients used for the preparation of the reference solid electrode include, for example, iron, molybdenum, chromium, tungsten, nickel, cobalt, silicon and manganese.

The finely divided metal or metal-metal oxide mixture may have incorporated therein a suitable amount of an anti-sintering material. By the incorporation of the anti-sintering material, the reference solid electrode material can be prevented from being excessively sintered in the sintering step, and the thermal expansion or contraction of the reference solid electrode can be made to be substantially the same as that of the solid electrolyte. Thus, the oxygen sensing element will not be distorted in the sintering step, and its high temperature durability increases. The antisintering material used includes, for example, stabilized zirconia ($ZrO_2$), which is usually identical to that used for the solid electrolyte material, and alumina ($Al_2O_3$), alumina-magnesia ($Al_2O_3.MgO$), silica ($SiO_2$) and alumina-silica ($Al_2O_3$-$SiO_2$). These antisintering materials may be used either alone or in combination.

The oxygen sensing element of the invention is advantageously used for measuring the content of oxygen, for example, in an exhaust gas from an automobile internal combustion engine or in a molten metal in the course of metal refining. It is particularly suitable for use in an exhaust gas purifying system wherein the content of oxygen in an exhaust gas from an automobile internal combustion engine is measured, thereby to determine the content of unburnt hydrocarbons, carbon monoxide and nitrogen oxides in the exhaust gas, the based on the measurement results, the air-fuel ratio is appropriately adjusted so that the efficiency of a catalyst for purifying the exhaust gas is enhanced.

Referring to FIGS. 6A and 6B there is disclosed an embodiment of the oxygen sensor device useful for measuring the content of oxygen in an exhaust gas from an automobile internal combustion engine. The oxygen sensor device is fitted to the exhaust manifold in a manner such that the external platinum electrode 6 of an oxygen sensing element 11 is exposed to the exhaust gas.

A casing 12 for protecting the oxygen sensing element 11 has a plurality of perforations through which the exhaust gas is allowed to flow. The output signals are transmitted from the respective electrodes through lead-out wires, such as a platinum lead 13 and a stainless steel lead 14, and to an electrical measuring circuit (not shown in FIGS. 6A and 6B). The output signal-taking out mechanism is electrically protected by an alumina tube 15, a Teflon tube 16 and an insulative tube 17 and is mechanically protected by metallic tubular members 18 and 19.

The invention will be further illustrated by way of the following example.

Example

A provisional solid electrolyte member 2 having a hole therein as illustrated in FIG. 1 was molded from a finely divided zirconia powder having incorporated therein 8% by mole of $Y_2O_3$. One end of a platinum lead-out wire having a diameter of 0.3 mm was inserted into a consolicated mass of a reference solid electrode material. The reference solid electrode material used was a mixture comprised of 40% by weight of a carbonyl iron powder, 20% by weight of a zirconia powder having incorporated therein 8% by mole of $Y_2O_3$ and 40% by weight of $NH_4HCO_3$. Then, the lead-out wire-inserted mass was compression-molded into a pellet of a columnar shape by using a hand press at a pressure of 600 kg/cm$^2$ for three minutes. The pellet so obtained was inserted in the hole of the provisional solid electrolyte member 2 in a mole 1 as illustrated in FIG. 2. A zirconia powder having incorporated therein 8% by mole of $Y_2O_3$ was piled up on the pellet-inserted provisional solid electrolyte member, and then, compression-molded by thrusting split plunging rods 6 into the mold 1, as illustrated in FIG. 3A. The compression molding was carried out by using a hand press at a pressure of 600 kg/cm$^2$ for three minutes. The molded product 8 of a columnar shape, so obtained, was demolded from the mold 1, and then, sintered at a temperature of 1,400° C. for three hours in an electric furnace while a hydrogen (1% by volume)-argon (99% by volume) gaseous mixture was introduced in the furnace at a rate of 1 liter/min. The sintered columnar pellet was treated with a concentrated hydrofluoric acid for five minutes and, then, washed. Thereafter, the pellet was coated with a platinum paste, and then, baked in an electric furnace at a temperature of 900° C. for ten minutes. The platinum electrode layer so formed had a thickness of approximately fine microns. The baked pellet was coated with a porous protective layer comprised of a spinel ($MgO.Al_2O_3$) by a plasma spraying technique. The porous protective layer had a thickness of approximately 100 microns.

The oxygen sensing element so prepared was tested for its electromotive force in an air atmosphere at a temperature of 500° C. by using a direct voltage indicator having an input impedance of 1 M-ohm. The electromotive force was about 0.99 V.

Following a procedure similar to that mentioned above, oxygen sensing elements were manufactured by using various reference solid electrode materials, and their electromotive forces were evaluated. The results are shown in the following table.

TABLE

| Run No. | Metal | Particle size of metal (microns) | Amount of metal (wt. %) | Amount of anti-sintering material* (wt. %) | Amount of $NH_4NHCO_3$ (wt. %) | Amount of $Y_2O_3$ incorporated in solid electrode metal (mole %) | Electro-motive force (V) |
|---|---|---|---|---|---|---|---|
| 1 | Fe | 10 | 40 | 20 | 40 | 5.5 | 0.99 |
| 2 | Ni | 10 | 50 | 20 | 30 | 5.5 | 0.92 |
| 3 | Co | 3 | 30 | 30 | 40 | 8.0 | 0.84 |
| 4 | Cr | 300 mesh | 40 | 40 | 20 | 8.0 | 1.03 |
| 5 | Mo | 0.5 | 30 | 20 | 50 | 10.0 | 0.95 |
| 6 | W | 5 | 40 | 20 | 40 | 10.0 | 0.79 |

*Anti-sintering material = same as the solid electrolyte material used

What we claim is:

1. A method of manufacturing an oxygen sensing element having a structure such that an external conductive metal electrode or electrodes are mounted on the exterior surface of a solid electrolyte member having totally embedded therein a means for providing a reference partial pressure of oxygen, said reference oxygen partial pressure-providing means being composed of a sintered product of a finely divided metal or metal-metal oxide mixture and having a lead-out wire connected thereto; said method comprising the steps of:
   (a) compression molding a part of the finely divided solid electrolyte material to form a provisional solid electrolyte member having a hole in which the reference oxygen partial pressure-providing means is to be formed;
   (b) forming in said hole of the provisional solid electrolyte member a provisional product of the reference oxygen partial pressure-providing means from the finely divided metal or metal-metal oxide mixture, said finely divided metal or metal-metal oxide mixture having incorporated therein an anti-sintering material in an amount sufficient for making the thermal expansion or contraction of the reference oxygen partial pressure means substantially the same as that of the said electrolyte members;
   (c) piling up the remaining part of the finely divided solid electrolyte material on the upper surface of the provisional reference oxygen partial pressure-providing means product and on the upper surface of the provisional solid electrolyte member, followed by compression molding the piled up solid electrolyte material to form an integrated structure comprising the solid electrolyte member having totally embedded therein the provisional reference oxygen partial pressure-providing means;
   (d) sintering the integrated structure in non-oxidizing atmosphere at a temperature of from approximately 1,350° to 1,500° C., and;
   (e) forming a layer or layers of the external conductive metal electrode or electrodes on at least a part of the exterior surface of the sintered integrated structure.

2. A method according to claim 1 wherein said formation of the provisional product of the reference oxygen partial pressure-providing means is carried out by a process in which the finely divided metal or metal-metal oxide mixture is filled in the hole of the provisional solid electrolyte member in the mold, and then, consolidated; and thereafter, the lead-out wire is fixed in the consolidated material.

3. A method according to claim 1 wherein said formation of the provisional product of the reference oxygen partial pressure-providing means is carried out by a process in which the finely divided metal or metal-metal oxide mixture is compression molded; the so molded product is inserted into the hole of the provisional solid electrolyte member in the mold; and then, the lead-out wire is fixed in the molded product.

4. A method according to claim 2 or 3 wherein, the remaining part of the finely divided solid electrolyte mateiral is piled up on the lead-out wire-fixed consolidated or molded product; and then, the piled up solid electrolyte material is compression-molded by thrusting into the mold split plunging rods having a narrow space formed therebetween in which the lead-out wire is fitted.

5. A method according to claim 1 wherein said steps of (b) and (c) are carried out by a process in which the finely divided metal or metal-metal oxide mixture is filled in the hole of the provisional solid electrolyte member in the mold; the remaining part of the finely divided solid electrolyte mateiral is piled up on the filled finely divided metal or metal-metal oxide mixture; a lead-out wire is inserted in the piled solid electrolyte mateiral; and then, the piled solid electrolyte material is compression-molded.

6. A method according to claim 1 wherein said steps of (b) and (c) are carried out by a process in which the finely divided metal or metal-metal oxide mixture is compression-molded; the so molded product is inserted in the hole of the provisional solid electrolyte member in the mold; the remianing part of the finely divided solid electrolyte material is piled up on the inserted product; a lead-out wire is inserted in the piled solid electrolyte mateiral; and then, the piled solid electrolyte mateiral is compression molded.